United States Patent [19]

Deberitz et al.

[11] Patent Number: 5,149,889
[45] Date of Patent: Sep. 22, 1992

[54] COMPOSITION FOR USE IN ORGANOLITHIUM SYNTHESIS REACTIONS

[75] Inventors: Jürgen Deberitz, Frankfurt; Wilfried Weiss, Oberursel, both of Fed. Rep. of Germany

[73] Assignee: Metallgesellschaft Aktiengesellschaft, Frankfurt am Main, Fed. Rep. of Germany

[21] Appl. No.: 605,742

[22] Filed: Oct. 30, 1990

Related U.S. Application Data

[63] Continuation-in-part of Ser. No. 346,868, May 3, 1989, Pat. No. 4,982,017.

[30] Foreign Application Priority Data

May 4, 1988 [DE] Fed. Rep. of Germany ....... 3815166

[51] Int. Cl.$^5$ .............. C07C 27/00; C07C 29/09; C07C 29/14
[52] U.S. Cl. .............. 568/878; 568/715; 568/821; 568/822; 568/823; 568/834; 568/838; 568/839; 568/846; 568/862; 568/876
[58] Field of Search .............. 568/715, 821, 822, 838, 568/839, 832, 834, 851, 846, 876, 878, 862

[56] References Cited

U.S. PATENT DOCUMENTS

| | | | |
|---|---|---|---|
| 3,087,896 | 4/1963 | Kamienski | 558/4 |
| 4,370,257 | 1/1983 | Imai et al. | 568/832 |
| 4,617,145 | 10/1986 | Schreiber et al. | 568/832 |
| 4,982,017 | 1/1991 | Deberitz et al. | 568/834 |

FOREIGN PATENT DOCUMENTS 3637780 11/1988 Fed. Rep. of Germany .

OTHER PUBLICATIONS

Bartlett et al., "Journal American Chemical," vol. 63: 3229-3230 (1941) QD1.A5.
"J. Amer. Chem. Soc.", vol. 85, pp. 1886-1887 (1963) Lansbury.

*Primary Examiner*—Werren B. Lone
*Attorney, Agent, or Firm*—Herbert Dubno; Jonathan Myers

[57] ABSTRACT

A process is disclosed for the preparation of tertiary alcohols, alpha-alkyl substituted nitriles, alkyl-substituted imines or tertiary amines by alkylation of a starting material that is a carbonyl compound or a nitrile followed by hydrolysis wherein the alkylation is carried out with the aid of a reaction system formed by suspending a mixture of:

substantially 15 to 25% by weight of methyllithium or ethyllithium;

substantially 35 to 45% by weight of an inorganic compound selected from the group which consists of at least one metal oxide selected from the group which consists of $SiO_2$, $Al_2O_3$, and $CaO$, and synthetic anhydrous aluminum silicate; and substantially 35 to 45% by weight of a paraffin oil or wax; in an organic solvent selected from the group which consists of:

$C_5$ to $C_{10}$ saturated aliphatic hydrocarbons, $C_5$ to $C_{10}$ cycloaliphatic hydrocarbons, aromatic hydrocarbons selected from the group which consists of benzene, toluene, and xylene, and aliphatic or cycloaliphatic ethers selected from the group which consists of diisopropyl ether, di-n-butyl ether, tert-butylether, tetrahydrofuran and dioxane.

12 Claims, No Drawings

COMPOSITION FOR USE IN ORGANOLITHIUM SYNTHESIS REACTIONS

CROSS REFERENCE TO RELATED APPLICATIONS

This application is a continuation-in-part of Ser. No. 07/346/868 filed May 2, 1989, now U.S. Pat. No. 4,982,017.

FIELD OF THE INVENTION

Our present invention relates to a method of alkylating an organic compound by a composition using a mixture, comprising an alkyllithium compound and an inert inorganic pulverulent carrier.

BACKGROUND OF THE INVENTION

Organolithium compounds play an important role in preparative organic chemistry when lithium or an organic substituent is to be incorporated in an organic compound.

The organolithium compounds are usually susceptible to reaction with air and moisture and, for this reason, may be handled only with precautions. For instance, butyllithium is a self-igniting liquid, which is susceptible to hydrolysis. For this reason, butyllithium is usually handled in 15 to 25% solutions, e.g. in alkanes, or in about 30% suspensions of paraffins (Römpp Chemie Lexikon, 8th edition, 1979, page 547). By contrast with their higher homologs, methyllithium and ethyllithium are insoluble or hardly soluble in saturated hydrocarbons and as solids are highly pyrophoric so that they ca be handled only with difficulty.

From Published German Application 36 37 780, it is known that the disadvantages of solutions of organomagnesium and organolithium compounds can be avoided by using them in pulverulent mixtures of clay dust and solutions of organomagnesium or organolithium compounds.

While the powders thus obtained are less susceptible to hydrolysis, they are pyrophoric, particularly with the organolithium compound.

In order to reduce their pyrophoric character, undesirably high clay contents are required, which in organic syntheses act as undesired accompanying substances and as sorbents.

In safety regulations for handling butyllithium, it has been stated that material which is flowing out can be treated with pulverulent limestone for preventing a fire. From "Synthesis" (1983), page 387, it is known to modify complex inorganic hydrides by incorporating them in silica gel or alumina.

The synthesis of methyllithium or ethyllithium is effected in a known manner, namely, methyllithium contained in diethyl ether o tetrahydrofuran and ethyllithium contained in hexane, by the reaction of lithium metal and alkyl halide in accordance with the formula:

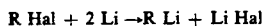

$$R\ Hal + 2\ Li \rightarrow R\ Li + Li\ Hal$$

Lithiummethyl has the highest solubility in diethyl ether, in which it has a solubility of about 5%. Solutions of ethyllithium have an ethyllithium concentration of about 2%. But the restriction to diethyl ether restricts the use of that compound, because numerous users hesitate to use diethyl ether on an industrial scale owing to its high vapor pressure and the formation of peroxide upon evaporation and try to avoid such use, if possible. In addition, the solutions have only relatively low concentrations.

OBJECTS OF THE INVENTION

It is an object of the invention to provide for synthesis reactions for incorporating lithium, a composition which has a higher content of the active compound but is non-pyrophoric and is susceptible to hydrolysis and can be used in the solvents usually employed in the chemistry of the organometallic compounds and can particularly be used in hydrocarbons.

Another object is to provide an improved reaction system for a metallization or alkylation reaction whereby earlier drawbacks are avoided.

It is also an object of our invention to provide an improved reaction method.

SUMMARY OF THE INVENTION

These objects are accomplished in accordance with the invention by providing a composition for synthesis reactions which is non-pyrophoric and flowable and consists essentially of:

(a) methyllithium or ethyllithium,
(b) one or more oxides of the group consisting of $SiO_2$, $Al_2O_3$, CaO and synthetic anhydrous aluminosilicate, and
(c) paraffin.

Solvent-free methyllithium or ethyllithium is a self-igniting solid so that these compounds can be handled only with difficulty.

While their pyrophoric character can be suppressed I5 by a mixing with paraffin, such as paraffin oil or paraffin waxes, a very high proportion of at least 60% will be required for that purpose. In reaction media, such as alkanes, such products consisting, e.g. of 60% solid paraffin and 40% methyllithium usually form thixotropic solutions. Mixtures with paraffin oils may become nonhomogeneous by segregation caused by sedimentation.

The composition for synthesis reactions in accordance with the invention is suitably a mixture composed of:

(a) 15 to 25%, preferably 18 to 22% by weight methyllithium or ethyllithium,
(b) 35 to 45%, preferably 38 to 42% by weight oxides of the group consisting of $SiO_2$, $Al_2O_3$, CaO and synthetic anhydrous aluminosilicate,
(c) 35 to 45%, preferably 38 to 42% by weight paraffin.

The method to alkylate an organic compound comprises the steps of:

(a) forming a reaction system by suspending a mixture of:

an alkyl-lithium component consisting of at least one alkyl-lithium compound;

an inorganic component selected from the group which consists of at least one oxide selected from the group which consists of $SiO_2$, $Al_2O_3$ and CaO, and synthetic anhydrous aluminum silicate; and a paraffinic component consisting of at least one paraffin compound in an organic solvent selected from the group which consists of:

$C_5$ to $C_{10}$ saturated aliphatic hydrocarbons, $C_5$ to $C_{10}$ cycloaliphatic hydrocarbons, aromatic hydrocarbons selected from the group which consists of benzene, toluene and xylene, and aliphatic or cycloaliphatic ethers selected from the group which consists of di-isopropylether, di-n-butylether, tert.-butylether, tetrahydrofuran and dioxane;

(b) treating said organic compound with said reaction system to form an alkylated product; and (c) recovering said alkylated product from said reaction system.

For the composition for synthesis reactions in accordance with the invention, it is essential that the carrier be inert relative to the alkyllithium compound. For this reason, the content of hydroxylic groups (usually derived from hydrating water) in the oxide of the carrier should not exceed 5% by weight. Any proton activity of the carrier will be indicated by an evolution of gas. For instance, methane will be evolved when a carrier which is still proton-active, such as silicon dioxide having an atmospheric moisture content, is introduced into the solution of the methyllithium.

The alkyllithium compound which is still in the solution from its production is absorbed by the particulate inert carrier. Upon removal of the solvent, a pyrophoric solid product will be obtained.

For this reason, it is a feature of the invention that the composition for use in synthesis reactions contains paraffin, which is a further component that is essential for the invention and shields the reactivity of the lithium compound from the atmosphere.

Suitable paraffins include solid, waxlike and liquid paraffins. In order to avoid an occasional occurrence of thixotropic effects in solvents, the composition for use in synthesis reactions in accordance with the invention preferably contains paraffin oil, particularly a viscous paraffin oil having a density of 0.860 to 0.892.

The composition for use in synthesis reactions in accordance with the invention permits the use of methyllithium and ethyllithium in solvents other than diethylether and hexane, respectively, which were previously available.

Such other solvents are saturated aliphatic or cycloaliphatic $C_5$-$C_{10}$ hydrocarbons, aromatic hydrocarbons of the group consisting of benzene, toluene, xylene, aliphatic or cycloaliphatic ethers of the group consisting of di-isopropylether, di-n-butylether, tert.-butylether, tetrahydrofuran, and dioxane.

When the composition for use in synthesis reactions in accordance with the invention is used for carrying out organolithium metallizing or alkylating reactions, the paraffin oil may be washed out with hydrocarbon solvents before the synthesis if this is required.

The reactivity may be somewhat lower than in ethereal solutions but this effect can be compensated by somewhat higher temperatures and/or longer-reaction times or by an addition of Lewis bases (tetrahydrofuran, tetramethylene diamine).

Desirable results will be produced by the carrier particularly in the hydrolytic processing of the reaction mixtures. For instance, sludges which can conveniently be separated will be obtained because surplus water will be absorbed by the carrier.

The composition for use in synthesis reactions in accordance with the invention is produced by known methods for the production of methyllithium or ethyllithium in diethyl ether and hexane, respectively.

The solution of 5% methyllithium in ether or the solution of 2% ethyllithium in hexane is charged under a protective gas atmosphere and with constant stirring into a reactor, which contains a mixture of paraffin oil and an anhydrous oxide, such as $SiO_2$, CaO or anhydrous synthetic aluminosilicate.

After homogenization in the liquid phase, ether is substantially removed from the mixture at 40° C. and under a reduced pressure of 700 mbars and the mixture is subsequently dried at 40° C. and 10 mbars. The dried product is granular and friable and is flowable. It will be understood that equal results will be obtained when the solution of methyllithium or ethyllithium is held in the reactor under a protective gas and the anhydrous oxide and the paraffin are charged into the solution individually or jointly and with stirring.

The advantages afforded by the composition for use in synthesis reactions in accordance with the invention are seen in that a pyrophoric organometallic solid is transformed to a non-pyrophoric form by the addition of paraffin and the non-pyrophoric material is rendered flowable by the further addition of an inert solid The composition for use in synthesis reactions which has been rendered inert and is non-pyrophoric, flowable and free of solvent is also eminently suitable for being transported and handled in organolithium syntheses.

The new method to alkylate organic compounds applies especially to carbonyl compounds such as aldehydes, ketones and carboxylic acids. Reaction temperature ranges from 0oC to the boiling point of the solvent. When the non-pyrophoric compositions containing methyllithium or ethyllithium are used to alkylate a ketone of the Formula (I)

R—CO—R$^1$ where R and R$^1$ each independently stand for $C_1$ to $C_6$ alkyl, phenyl or phenyl-$C_1$ to $C_4$ alkyl, preferably benzyl or R and R$^1$ together with the adjacent carbon atom form a carbocyclic ring containing 4 to 7 carbon atoms, i.e. cyclobutyl, cyclpentyl, cyclohexyl or cycloheptyl, the product is a tertiary alcohol of the Formula (II)

$$R-\underset{\underset{R^2}{|}}{\overset{\overset{OH}{|}}{C}}-R^1$$

wherein R2 is methyl or ethyl.

When the non-pyrophoric compositions containing methyllithium or ethyllithium are used to alkylate an aldehyde of the Formula (III)

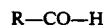

R—CO—H where R is $C_1$ to $C_6$ alkyl, phenyl or phenyl-$C_1$ to $C_4$ alkyl, preferably benzyl, the product is a tertiary alcohol of the Formula (IV)

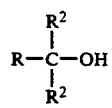

$$R-\underset{\underset{R^2}{|}}{\overset{\overset{R^2}{|}}{C}}-OH$$

ps wherein R$^2$ is methyl or ethyl. In the case of the ketone of the Formula (I) one mole of the methyllithium or ethyllithium and one mole of water are required per mole of ketone. In the case of the aldehyde of the Formula (III), two moles of the methyllithium or ethyllithium and one mole of water are required per mole of the aldehyde or in other words one-half of the stoichiometric amount of the aldehyde is employed per the amount of methyllithium or ethyllithium.

Thus the reaction of the ketone of the Formula (I) and the methyllithium or ethyllithium proceeds as follows:

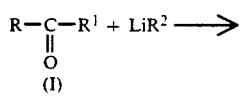

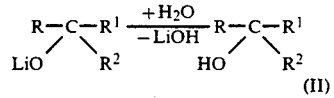

The reaction of the aldehyde of the Formula (III) and the methyllithium or ethyllithium proceeds as follows:

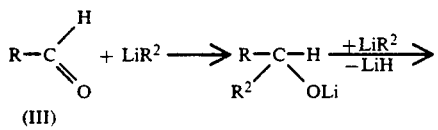

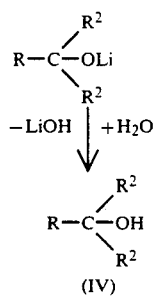

When the non-pyrophoric compositions containing methyllithium or ethyllithium are used to alkylate a carboxylic acid of the Formula (V)

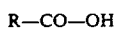

where R is $C_1$ to $C_6$ alkyl, phenyl or phenyl-$C_1$ to $C_4$ alkyl, preferably benzyl, to yield the tertiary alcohol of the Formula (IV), two moles of the methyllithium or ethyllithium are required as well as one mole of water per mole of the carboxylic acid. The reaction of the carboxylic acid of the Formula (V) and the methyllithium or ethyllithium proceeds as follows:

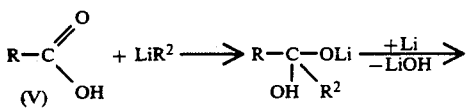

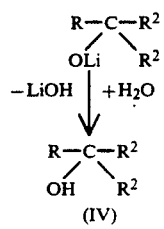

When the non-pyrophoric compositions containing methyllithium or ethyllithium are used to alkylate a nitrile having an alpha-hydrogen of the Formula (VI)

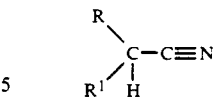

where R and $R^1$ each independently stand for $C_1$ to $C_6$ alkyl, phenyl or phenyl-$C_1$ to $C_4$ alkyl, preferably benzyl or R and $R^1$ together with the adjacent alpha-carbon form a carbocyclic ring containing 4 to 7 carbon atoms, i.e. cyclobutyl, cyclpentyl, cyclohexyl or cycloheptyl, to yield a tertiary nitrile of the Formula (VII) having an alpha-methyl or alpha-ethyl group:

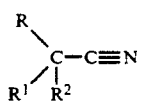

One mole of the methyllithium or ethyllithium is required per mole of the nitrile of the Formula (VI).

The reaction of the nitrile of the Formula (VI) and the methyllithium or ethyllithium proceeds as follows:

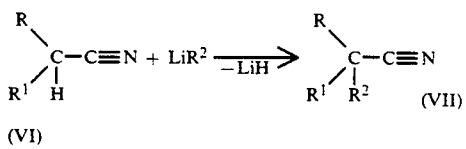

When one mole of methyllithium or ethyllithium contained in the non-pyrophoric composition is used to alkylate a nitrile of the Formula (VIII) having no alpha-carbon atom $$R^3-C\equiv N$$

wherein $R^3$ is tertiary-butyl or phenyl the product obtained is either a methylated- or ethylated-imine of the Formula (IXa)

where $R^2$ is methyl or ethyl. The imine of the Formula (IXa) may then be hydrolyzed to form a ketone of the Formula (IXb) as well as the liberation of ammonia:

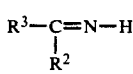

However, when two moles of the methyllithium or ethyllithium in the non-pyrophoric composition are employed per mole of the starting nitrile of the Formula (VIII), the product obtained is a tertiary amine of the Formula (IXc)

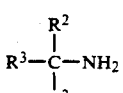

where again $R^2$ is methyl or ethyl.

The reaction scheme for a nitrile of the Formula (VIII) and methyllithium or ethyllithium proceeds as follows:

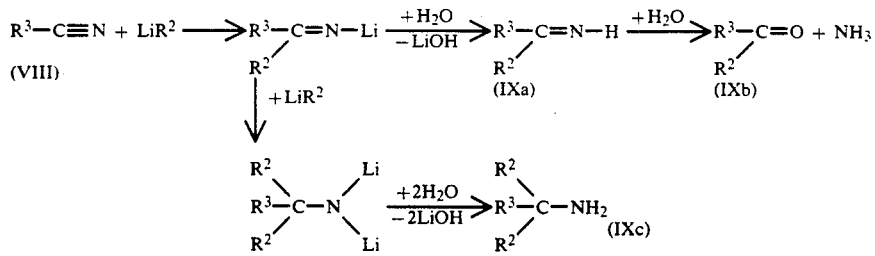

SPECIFIC EXAMPLES

The invention will be explained in greater detail with reference to the following Examples.

EXAMPLE 1

This control example shows that a product of methyllithium and paraffin alone does not have satisfactory properties.

12 g paraffin oil having a density of 0.865 were added under a protective gas and with stirring to 200 ml of a solution of 5% methyllithium in diethyl ether. The mixture was homogenized and subsequently the ether was removed from the mixture at 40° C. and 700 mbars and with constant stirring and was dried at 40° C. and 10 mbars with continued stirring for about 60 minutes. The resulting product was composed of 37% by weight methyllithium and 63% paraffin oil and had a friable, but sticky consistency and did not exhibit pyrophoric properties. Products which were friable and flowable were obtained from similar mixtures which contained solid paraffin waxes but their use in organolithium syntheses involved difficulties in processing because thixotropic solutions formed in the reaction media.

For production of a flowable, non-pyrophoric composition for use in synthesis reactions, 67.4 g $Al_2O_3$ (water content 0.5%, particle size 60 to 100 μm) and 69.7 g paraffin oil having a density of 0.865 were charged into a flashlike reactor and were mixed with stirring.

Under a protective gas and with constant stirring, 1000 ml of a solution of 5.6% methyllithium in diethyl ether were then charged. 7.3 liters methane were evolved during the addition. The temperature rose by 4° C. from an initial value of 20° C.

Substantially all diethyl ether was removed from the resulting suspension at 40° C. and 700 mbars under a protective atmosphere and with constant stirring and the suspension was subsequently evaporated to dryness at 40° C. and 10 mbars for about 60 minutes. The product now obtained was friable, flowable and non-pyrophoric. When the white product is stored in the air, it will not ignite but will slowly lose its activity and assume a yellowish color.

An analysis of the freshly produced product indicated a total basicity of 20.42% and an active basicity of 16.70%. The "active basicity" is the content of active R-Li in the compound, as determined in accordance with Zerewitinow; and the "total basicity" is the content of active R-L plus other lithium bases (Li-OR, Li-OH) calculated as LiOH and determined by titrimetry.

EXAMPLE 3

For the production of another flowable and non-pyrophoric composition for use in synthesis reactions, 34.1 g of a synthetic anhydrous aluminosilicate having a particle size of 10 to 100 μm 94.1 g paraffin oil having a density of 0 865 were mixed with stirring in a flashlike reactor and were then mixed and homogenized under a protective gas atmosphere with 1000 ml of a solution of 5.3% ethyllithium in diethyl ether at 20° C. The temperature rose by 1° C. and 2100 ml methane were evolved.

Substantially all diethyl ether was then removed from the resulting suspension at 40° C. and 700 mbars with stirring while the protective gas atmosphere was maintained. The suspension was subsequently evaporated to dryness with constant stirring at 40° C. and 10 mbars for about 60 minutes. The resulting product was friable, flowable and non-pyrophoric. An analysis of the freshly produced product indicated a total basicity of 22.36% and an active basicity of 20.37.

Similar results are produced when CaO is used as a carrier in Examples 2 and 3. The contents of lithium compound and paraffin oil will depend on the particle size of the carrier and on the surface area which is available. The larger the surface area of the carrier, the higher will be the content of the lithium compound which is taken-up and the required content of paraffin oil, within the limits stated.

The average content of the lithium compound in the carrier usually amounted to about 20 to 25%.

EXAMPLE 4

In this example, the alkylation of cyclohexanone with the aid of the composition for synthesis reactions in accordance with the invention will be described.

For that purpose, a mixture having the following composition and suspended in 400 ml n-pentane was charged under a nitrogen atmosphere into a reactor provided with a dripping funnel, stirrer and reflux condenser:

22.9% methyllithium (R-Li content 340 mmol)
39.1% paraffin oil (density 0.865)
37.9% $Al_2O_3$ (water content 0.5%)

360 mmol cyclohexanone was added at a controlled rate during 100 minutes. This resulted in a temperature rise to 29° C. The reaction mixture was maintained at 36° C. for a further two hours under reflux conditions. The reaction mixture was subsequently hydrolyzed by an addition of 12 g water with cooling. The properly settling precipitate was filtered off and the pentane was removed from the precipitate by distillation. 60.5 g of a crude product were obtained, in which the ratio of cyclohexanone to 1-methylcyclohexanol amounted to 9.6:90.4. 1-methylcyclohexanol was isolated by distillation.

EXAMPLE 5

In this example the alkylation of benzaldehyde with the aid of the composition for synthesis reactions in accordance with the invention is described.

The same procedures and reaction conditions as set forth in Example 4 are employed here, except that the starting material is benzaldehyde instead of cyclohexanone. Furthermore 2 moles of the methyllithium are employed per mole of benzaldehyde instead of one mole of cyclohexanone as per Example 4. The product obtained is alpha-1,1-dimethyl-benzyl alcohol.

EXAMPLE 6

The same procedures and reaction conditions as set forth in Example 4 are employed here, except that the starting material is acetic acid instead of cyclohexanone. Furthermore 2 moles of the methyllithium are employed per mole of acetic acid instead of one mole of cyclohexanone as in Example 4. The product obtained is tertiary-butyl alcohol.

EXAMPLE 7

The same procedures and reaction conditions as set forth in Example 4 are employed here, except that the starting material is benzyl cyanide instead of cyclohexanone. The product obtained is alpha-methyl-benzyl cyanide.

EXAMPLE 8

The same procedures and reaction conditions as set forth in Example 4 are employed here, except that the starting material is phenyl cyanide instead of cyclohexanone. One mole of methyllithium is employed per mole of phenyl cyanide. After hydrolysis, the product obtained is alpha-methyl-benzyl imine which upon further hydrolysis yields phenylmethyl ketone and ammonia

EXAMPLE 9

The same procedures and reaction conditions as set forth in Example 8 are employed here, except that 2 moles of methyllithium are employed per mole of phenyl cyanide Following hydrolysis, the product obtained is 1,1-di-alpha-methyl-benzyl amine.

What is claimed is:

1. A process for preparing a tertiary alcohol of the Formula (II)

wherein

R and $R^1$ are each independently $C_1$ to $C_6$ alkyl, phenyl, or phenyl-$C_1$ to $C_4$ alkyl, or R and $R^1$ together with the adjacent carbon atom form a $C_4$ to $C_7$ carbocyclic ring, and $R^2$ is methyl or ethyl, which comprises the steps of:

(a) forming a reaction system by suspending a mixture of:
   15 to 25% by weight of methyllithium or ethyllithium;
   35 to 45% by weight of an inorganic compound selected from the group which consists of at least one metal oxide selected from the group which consists of $SiO_2$, $Al_2O_3$, and CaO, and synthetic anhydrous aluminum silicate; and
   35 to 45% by weight of a paraffin oil or wax; in an organic solvent selected from the group which consists of:
   $C_5$ to $C_{10}$ saturated aliphatic hydrocarbons, $C_5$ to $C_{10}$ cycloaliphatic hydrocarbons, aromatic hydrocarbons selected from the group which consists of benzene, toluene, and xylene, and aliphatic or cycloaliphatic ethers selected from the group which consists of diisopropyl ether, di-n-butyl ether, tert-butylether, tetrahydrofuran and dioxane;

(b) adding a ketone of the Formula (I)

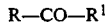

to said reaction system at a temperature between 0° C. and the boiling point of the organic solvent in an amount that is stoichiometrically equivalent to the amount of methyllithium or ethyllithium in the reaction system and refluxing said reaction system to form a reaction product;

(c) hydrolyzing and cooling the reaction product formed in step (b) by adding water to the reaction system to form the tertiary alcohol of the Formula (II); and (d) recovering the tertiary alcohol of the Formula (II) from the reaction system.

2. The process defined in claim 1 wherein said mixture consists essentially of:
   18 to 22% by weight of methyllithium or ethyllithium;
   38 to 42% by weight of said inorganic compound; and
   38 to 42% by weight of paraffin oil or wax.

3. The process defined in claim 1 wherein hydroxyl group content of said inorganic compound is no more than 5% by weight.

4. The process defined in claim 1 wherein said paraffin oil has a density of 0.7860 to 0.892.

5. A process for preparing a tertiary alcohol of the Formula (IV)

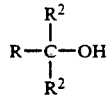

wherein

R is $C_1$ to $C_6$ alkyl, phenyl, or phenyl-$C_1$ to $C_4$ alkyl, and $R^2$ is methyl or ethyl, which comprises the steps of:

(a) forming a reaction system by suspending a mixture of:
   15 to 25% by weight of methyllithium or ethyllithium;
   35 to 45% by weight of an inorganic compound selected from the group which consists of at least one metal oxide selected from the group which consists of $SiO_2$, $Al_2O_3$, and CaO, and synthetic anhydrous aluminum silicate; and
   35 to 45% by weight of a paraffin oil or wax; in an organic solvent selected from the group which consists of:
   $C_5$ to $C_{10}$ saturated aliphatic hydrocarbons, $C_5$ to $C_{10}$ cycloaliphatic hydrocarbons, aromatic hydrocarbons selected from the group which consists of benzene, toluene, and xylene, and aliphatic or cycloaliphatic ethers selected from the group which consists of diisopropyl ether, di-n-butyl ether, tert-butylether, tetrahydrofuran and dioxane;

(b) adding a ketone of the Formula (III)

R—CO—H to said reaction system at a temperature between 0° C. and the boiling point of the organic solvent in an amount that is stoichiometrically equivalent to one-half of the amount of methyllithium or ethyllithium in the reaction system and refluxing said reaction system to form a reaction product;

(c) hydrolyzing and cooling the reaction product formed in step (b) by adding water to the reaction system to form the tertiary alcohol of the Formula (IV); and (d) recovering the tertiary alcohol of the Formula (IV) from the reaction system.

6. The process defined in claim 5 wherein said mixture consists essentially of:
   18 to 22% by weight of methyllithium or ethyllithium;
   38 to 42% by weight of said inorganic compound; and
   38 to 42% by weight of paraffin oil or wax.

7. The process defined in claim 5 wherein hydroxyl group content of said inorganic compound is no more than 5% by weight.

8. The process defined in claim 5 wherein said paraffin oil has a density of 0.860 to 0.892.

9. A process for preparing a tertiary alcohol of the Formula (IV)

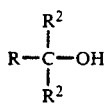

wherein
R is $C_1$ to $C_6$ alkyl, phenyl, or phenyl-$C_1$ to $C_4$ alkyl, and
$R^2$ is methyl or ethyl, which comprises the steps of:
(a) forming a reaction system by suspending a mixture of:
   15 to 25% by weight of methyllithium or ethyllithium;
   35 to 45% by weight of an inorganic compound selected from the group which consists of at least one metal oxide selected from the group which consists of $SiO_2$, $Al_2O_3$, and CaO, and synthetic anhydrous aluminum silicate; and
   35 to 45% by weight of a paraffin oil or wax; in an organic solvent selected from the group which consists of:
   $C_5$ to $C_{10}$ saturated aliphatic hydrocarbons, $C_5$ to $C_{10}$ cycloaliphatic hydrocarbons, aromatic hydrocarbons selected from the group which consists of benzene, toluene, and xylene, and aliphatic or cycloaliphatic ethers selected from the group which consists of diisopropyl ether, di-n-butyl ether, tert-butylether, tetrahydrofuran and dioxane;

(b) adding a ketone of the Formula (V)

R—CO—OH to said reaction system at a temperature between 0° C. and the boiling point of the organic solvent in an amount that is stoichiometrically equivalent to one-half of the amount of methyllithium or ethyllithium in the reaction system and refluxing said reaction system to form a reaction product;

(c) hydrolyzing and cooling the reaction product formed in step (b) by adding water to the reaction system to form the tertiary alcohol of the Formula (IV); and (d) recovering the tertiary alcohol of the Formula (IV) from the reaction system.

10. The process defined in claim 9 wherein said mixture consists essentially of:
    18 to 22% by weight of methyllithium or ethyllithium;
    38 to 42% by weight of said inorganic compound; and
    38 to 42% by weight of paraffin oil or wax.

11. The process defined in claim 9 wherein hydroxyl group content of said inorganic compound is no more than 5% by weight.

12. The process defined in claim 9 wherein said paraffin oil has a density of 0.860 to 0.892.

* * * * *